United States Patent
Buiser et al.

(10) Patent No.: US 7,094,369 B2
(45) Date of Patent: Aug. 22, 2006

(54) PROCESSES FOR MANUFACTURING POLYMERIC MICROSPHERES

(75) Inventors: Marcia Buiser, Watertown, MA (US); Samuel P. Baldwin, Newton, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 421 days.

(21) Appl. No.: 10/109,966

(22) Filed: Mar. 29, 2002

(65) Prior Publication Data

US 2003/0183962 A1 Oct. 2, 2003

(51) Int. Cl.
*B29B 9/00* (2006.01)

(52) U.S. Cl. .................. 264/7; 264/5; 427/212
(58) Field of Classification Search ........... 264/4.6, 264/5, 7, 15; 427/212
See application file for complete search history.

(56) References Cited

U.S. PATENT DOCUMENTS

| | | |
|---|---|---|
| 2,275,154 A | 3/1942 | Merrill et al. |
| 2,609,347 A | 9/1952 | Wilson |
| 3,663,470 A | 5/1972 | Nishimura et al. |
| 3,737,398 A | 6/1973 | Yamaguchi |
| 3,957,933 A | 5/1976 | Egli et al. |
| 4,025,686 A | 5/1977 | Zion |
| 4,034,759 A | 7/1977 | Haerr |
| 4,055,377 A | 10/1977 | Erickson et al. |
| 4,076,640 A | 2/1978 | Forgensi et al. |
| 4,094,848 A | 6/1978 | Naito |

(Continued)

FOREIGN PATENT DOCUMENTS

| | | |
|---|---|---|
| AU | A-76186/98 | 10/1998 |
| DE | 3834705 | 4/1990 |
| DE | 9414868.6 | 9/1994 |
| DE | 94 14 868.6 | 2/1995 |
| DE | 100 26 620 | 5/2000 |
| DE | 297 24 255 U1 | 10/2000 |
| DE | 100 26 620 A 1 | 3/2002 |
| EP | 0 067 459 A1 | 12/1982 |
| EP | 0122624 | 10/1984 |
| EP | 0123235 | 10/1984 |

(Continued)

OTHER PUBLICATIONS

Markus, H.S., "Experimental Aspects of High–Intensity Transient Signals in the Detection of Emboli," *J Clin Ultrasound* 23:81–87 (1995).

Schwarz, K.Q., "The Acoustic Filter: An Ultrasonic Blood Filter for the Heart–Lung Machine," *Journal of Thoracic and Cardiovascular Surgery* 104(6):1647–1653 (1992).

Chuang et al., "Experimental Canine Hepatic Artery Embolization with Polyvinyl Alcohol Foam Particles," Departments of Diagnostic Radiology and Veterinary Medicine, The University of Texas, M.D. Anderson Hospital and Tumor Institute at Houston, Houston, Texas, pp. 21–25.

Kerber, "Flow–Controlled Therapeutic Embolization: A Physiologic and Safe Technique," *AJR,* Mar., 1980, vol. 134, pp. 557–561.

(Continued)

*Primary Examiner*—Mary Lynn Theisen
(74) *Attorney, Agent, or Firm*—Fish & Richardson P.C.

(57) ABSTRACT

Processes of manufacturing polymeric microspheres facilitate the generation of polymeric microspheres of size ranges smaller than 600 microns diameter by forming beads of a predetermined size from a starting material which may include a template polymer, and subsequently contacting the beads with a structural polymer. After crosslinking of the structural polymer has taken place, the template polymer may be removed to form the finished microspheres.

57 Claims, 2 Drawing Sheets

U.S. PATENT DOCUMENTS

| | | | |
|---|---|---|---|
| 4,096,230 A | 6/1978 | Haerr | |
| 4,098,728 A | 7/1978 | Rosenblatt | 521/141 |
| 4,110,529 A | 8/1978 | Stoy | 528/491 |
| 4,159,719 A | 7/1979 | Haerr | |
| 4,191,672 A | 3/1980 | Salome et al. | 260/29.6 |
| 4,198,318 A | 4/1980 | Stowell et al. | |
| 4,243,794 A | 1/1981 | White et al. | |
| 4,246,208 A | 1/1981 | Dundas | |
| 4,266,030 A | 5/1981 | Tschang et al. | |
| 4,268,495 A | 5/1981 | Muxfeldt et al. | |
| 4,271,281 A | 6/1981 | Kelley et al. | 526/80 |
| 4,402,319 A | 9/1983 | Handa et al. | |
| 4,413,070 A | 11/1983 | Rembaum | 523/223 |
| 4,427,794 A | 1/1984 | Lange et al. | 521/28 |
| 4,428,869 A | 1/1984 | Munteanu et al. | |
| 4,429,062 A | 1/1984 | Pasztor et al. | |
| 4,442,843 A | 4/1984 | Rasor et al. | |
| 4,444,961 A | 4/1984 | Timm | 526/88 |
| 4,452,773 A | 6/1984 | Molday | 424/1.1 |
| 4,456,693 A | 6/1984 | Welsh | |
| 4,459,145 A | 7/1984 | Elsholz | |
| 4,472,552 A | 9/1984 | Blouin | 525/61 |
| 4,477,255 A | 10/1984 | Pasztor et al. | |
| 4,492,720 A | 1/1985 | Mosier | 427/213.3 |
| 4,522,953 A | 6/1985 | Barby et al. | |
| 4,542,178 A | 9/1985 | Zimmermann et al. | 524/388 |
| 4,551,132 A | 11/1985 | Pasztor et al. | |
| 4,551,436 A | 11/1985 | Johnson et al. | |
| 4,573,967 A | 3/1986 | Hargrove et al. | |
| 4,622,362 A | 11/1986 | Rembaum | 525/54.1 |
| 4,623,706 A | 11/1986 | Timm et al. | 526/88 |
| 4,640,807 A | 2/1987 | Afghan et al. | |
| 4,657,756 A | 4/1987 | Rasor et al. | |
| 4,661,137 A | 4/1987 | Garnier et al. | 65/21.4 |
| 4,663,358 A | 5/1987 | Hyon et al. | 521/64 |
| 4,671,954 A | 6/1987 | Goldberg et al. | 424/450 |
| 4,674,480 A | 6/1987 | Lemelson | |
| 4,675,113 A | 6/1987 | Graves et al. | |
| 4,678,710 A * | 7/1987 | Sakimoto et al. | 428/407 |
| 4,678,814 A | 7/1987 | Rembaum | 522/175 |
| 4,680,320 A | 7/1987 | Uku et al. | 523/313 |
| 4,681,119 A | 7/1987 | Rasor et al. | |
| 4,695,466 A | 9/1987 | Morishita et al. | |
| 4,713,076 A | 12/1987 | Draenert | |
| 4,742,086 A | 5/1988 | Masamizu et al. | |
| 4,743,507 A | 5/1988 | Franses et al. | 428/402 |
| 4,772,635 A | 9/1988 | Mitschker et al. | 521/34 |
| 4,782,097 A | 11/1988 | Jain et al. | 521/56 |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | 424/443 |
| 4,804,366 A | 2/1989 | Zdeb et al. | |
| 4,819,637 A | 4/1989 | Dormandy, Jr. et al. | |
| 4,822,535 A | 4/1989 | Ekman et al. | 264/4.3 |
| 4,833,237 A | 5/1989 | Kawamura et al. | 536/20 |
| 4,850,978 A | 7/1989 | Dudar et al. | |
| 4,859,711 A | 8/1989 | Jain et al. | 521/56 |
| 4,863,972 A | 9/1989 | Itagaki et al. | 521/141 |
| 4,897,255 A | 1/1990 | Fritzberg et al. | |
| 4,929,400 A | 5/1990 | Rembaum et al. | 264/10 |
| 4,933,372 A | 6/1990 | Feibush et al. | |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | 424/449 |
| 4,999,188 A | 3/1991 | Solodovnik et al. | 424/78 |
| 5,007,940 A | 4/1991 | Berg | 623/66 |
| 5,011,677 A | 4/1991 | Day et al. | |
| H915 H | 5/1991 | Gibbs | |
| 5,015,423 A | 5/1991 | Eguchi et al. | |
| 5,032,117 A | 7/1991 | Motta | |
| 5,034,324 A | 7/1991 | Shinozaki et al. | 435/178 |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | 524/458 |
| 5,114,421 A | 5/1992 | Polak | |
| 5,116,387 A | 5/1992 | Berg | 623/66 |
| 5,120,349 A | 6/1992 | Stewart et al. | 71/93 |
| 5,125,892 A | 6/1992 | Drudik | |
| 5,147,631 A | 9/1992 | Glajch et al. | |
| 5,147,937 A | 9/1992 | Frazza et al. | 525/243 |
| 5,149,543 A | 9/1992 | Cohen et al. | 424/499 |
| 5,158,573 A | 10/1992 | Berg | 623/66 |
| 5,171,214 A | 12/1992 | Kolber et al. | |
| 5,181,921 A | 1/1993 | Makita et al. | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | 526/201 |
| 5,253,991 A | 10/1993 | Yokota et al. | |
| 5,260,002 A | 11/1993 | Wang | 264/4.1 |
| 5,262,176 A | 11/1993 | Palmacci et al. | 424/9 |
| 5,263,992 A | 11/1993 | Guire | |
| 5,288,763 A | 2/1994 | Li et al. | 521/61 |
| 5,292,814 A | 3/1994 | Bayer et al. | |
| 5,302,369 A | 4/1994 | Day et al. | |
| 5,314,974 A | 5/1994 | Ito et al. | |
| 5,316,774 A | 5/1994 | Eury et al. | 424/426 |
| RE34,640 E | 6/1994 | Kennedy et al. | |
| 5,320,639 A | 6/1994 | Rudnick | |
| 5,328,936 A | 7/1994 | Leifholtz et al. | |
| 5,336,263 A | 8/1994 | Ersek et al. | |
| 5,344,452 A | 9/1994 | Lemperle | 623/11 |
| 5,344,867 A | 9/1994 | Morgan et al. | 524/460 |
| 5,354,290 A | 10/1994 | Gross | 604/367 |
| 5,369,133 A | 11/1994 | Ihm et al. | 521/53 |
| 5,369,163 A | 11/1994 | Chiou et al. | 524/458 |
| 5,382,260 A | 1/1995 | Dormandy, Jr. et al. | |
| 5,384,124 A | 1/1995 | Courteille et al. | 424/430 |
| 5,397,303 A | 3/1995 | Sancoff et al. | |
| 5,398,851 A | 3/1995 | Sancoff et al. | |
| 5,403,870 A | 4/1995 | Gross | 523/105 |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,456,693 A | 10/1995 | Conston et al. | |
| 5,468,801 A | 11/1995 | Antonelli et al. | 524/504 |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | 424/489 |
| 5,494,940 A | 2/1996 | Unger et al. | 521/66 |
| 5,512,604 A | 4/1996 | Demopolis | |
| 5,514,090 A | 5/1996 | Kriesel et al. | |
| 5,525,334 A | 6/1996 | Ito et al. | |
| 5,534,589 A | 7/1996 | Hager et al. | |
| 5,541,031 A | 7/1996 | Yamashita et al. | 430/109 |
| 5,542,935 A | 8/1996 | Unger et al. | |
| 5,553,741 A | 9/1996 | Sancoff et al. | |
| 5,556,610 A | 9/1996 | Yan et al. | |
| 5,556,931 A | 9/1996 | Cercone et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,567,415 A | 10/1996 | Porter | |
| 5,569,193 A | 10/1996 | Hofstetter et al. | |
| 5,569,449 A | 10/1996 | Klaveness et al. | |

| Patent No. | Date | Name | Ref. |
|---|---|---|---|
| 5,569,468 A | 10/1996 | Modi | |
| 5,571,182 A | 11/1996 | Ersek et al. | 623/11 |
| 5,583,162 A | 12/1996 | Li et al. | 521/56 |
| 5,585,112 A | 12/1996 | Unger et al. | |
| 5,595,821 A | 1/1997 | Hager et al. | |
| 5,622,657 A | 4/1997 | Takada et al. | |
| 5,624,685 A | 4/1997 | Takahashi et al. | |
| 5,635,215 A | 6/1997 | Boschetti et al. | 424/501 |
| 5,637,087 A | 6/1997 | O'Neil et al. | |
| 5,639,710 A | 6/1997 | Lo et al. | 504/116 |
| 5,648,095 A | 7/1997 | Illum et al. | 424/489 |
| 5,648,100 A | 7/1997 | Boschetti et al. | 424/501 |
| 5,650,116 A | 7/1997 | Thompson | 264/561 |
| 5,651,990 A | 7/1997 | Takada et al. | |
| 5,653,922 A | 8/1997 | Li et al. | 264/4.3 |
| 5,657,756 A | 8/1997 | Vrba | |
| 5,681,576 A | 10/1997 | Henry | |
| 5,695,480 A | 12/1997 | Evans et al. | |
| 5,695,740 A | 12/1997 | Porter | |
| 5,698,271 A | 12/1997 | Liberti et al. | 427/550 |
| 5,701,899 A | 12/1997 | Porter | |
| 5,716,981 A | 2/1998 | Hunter et al. | |
| 5,718,884 A | 2/1998 | Klaveness et al. | |
| 5,723,269 A | 3/1998 | Akagi et al. | |
| 5,725,534 A | 3/1998 | Rasmussen | |
| 5,733,925 A | 3/1998 | Kunz et al. | |
| 5,741,331 A | 4/1998 | Pinchuk | |
| 5,746,734 A | 5/1998 | Dormandy, Jr. et al. | |
| 5,752,974 A | 5/1998 | Rhee et al. | 606/214 |
| 5,756,127 A | 5/1998 | Grisoni et al. | |
| 5,760,097 A | 6/1998 | Li et al. | 521/61 |
| 5,766,147 A | 6/1998 | Sancoff et al. | |
| 5,770,222 A | 6/1998 | Unger et al. | |
| 5,779,668 A | 7/1998 | Grabenkort | |
| 5,785,642 A | 7/1998 | Wallace et al. | |
| 5,785,682 A | 7/1998 | Grabenkort | |
| 5,792,478 A | 8/1998 | Lawin et al. | |
| 5,795,562 A | 8/1998 | Klaveness et al. | |
| 5,797,953 A | 8/1998 | Tekulve | |
| 5,807,323 A | 9/1998 | Kriesel et al. | |
| 5,813,411 A | 9/1998 | Van Bladel et al. | |
| 5,823,198 A | 10/1998 | Jones et al. | |
| 5,827,502 A | 10/1998 | Klaveness et al. | |
| 5,827,531 A | 10/1998 | Morrison et al. | 424/450 |
| 5,830,178 A | 11/1998 | Jones et al. | |
| 5,833,361 A | 11/1998 | Funk | |
| 5,840,387 A | 11/1998 | Berlowitz-Tarrant et al. | |
| 5,846,518 A | 12/1998 | Yan et al. | |
| 5,855,615 A | 1/1999 | Bley et al. | |
| 5,863,957 A | 1/1999 | Li et al. | 521/61 |
| 5,876,372 A | 3/1999 | Grabenkort et al. | |
| 5,877,224 A | 3/1999 | Brocchini et al. | |
| 5,885,216 A | 3/1999 | Evans, III et al. | |
| 5,885,547 A | 3/1999 | Gray | 424/1.37 |
| 5,888,930 A | 3/1999 | Smith et al. | |
| 5,891,155 A | 4/1999 | Irie | |
| 5,895,398 A | 4/1999 | Wensel et al. | |
| 5,895,411 A | 4/1999 | Irie | |
| 5,899,877 A | 5/1999 | Leibitzki et al. | |
| 5,902,832 A | 5/1999 | Van Bladel et al. | |
| 5,902,834 A | 5/1999 | Porrvik | |
| 5,922,025 A | 7/1999 | Hubbard | |
| 5,928,626 A | 7/1999 | Klaveness et al. | |
| 5,951,160 A | 9/1999 | Ronk | |
| 5,959,073 A | 9/1999 | Schlameus et al. | 528/490 |
| 6,003,566 A | 12/1999 | Thibault et al. | |
| 6,015,546 A | 1/2000 | Sutton et al. | |
| 6,027,472 A | 2/2000 | Kriesel et al. | |
| 6,028,066 A | 2/2000 | Unger | |
| 6,047,861 A | 4/2000 | Vidal et al. | |
| 6,048,908 A | 4/2000 | Kitagawa | |
| 6,051,247 A | 4/2000 | Hench et al. | 424/423 |
| 6,056,721 A | 5/2000 | Shulze | |
| 6,056,844 A | 5/2000 | Guiles et al. | |
| 6,059,766 A | 5/2000 | Greff | |
| 6,063,068 A | 5/2000 | Fowles et al. | |
| 6,071,497 A | 6/2000 | Steiner et al. | 424/45 |
| 6,073,759 A | 6/2000 | Lamborne et al. | |
| 6,090,925 A | 7/2000 | Woiszwillo et al. | 530/410 |
| 6,096,344 A | 8/2000 | Liu et al. | 424/501 |
| 6,099,864 A | 8/2000 | Morrison et al. | |
| 6,100,306 A | 8/2000 | Li et al. | 521/61 |
| 6,139,963 A | 10/2000 | Fujii et al. | |
| 6,149,623 A | 11/2000 | Reynolds | |
| 6,160,084 A | 12/2000 | Langer et al. | |
| 6,162,377 A | 12/2000 | Ghosh et al. | |
| 6,165,193 A | 12/2000 | Greene, Jr. et al. | |
| 6,179,817 B1 | 1/2001 | Zhong | |
| 6,191,193 B1 | 2/2001 | Lee et al. | 523/201 |
| 6,214,331 B1 | 4/2001 | Vanderhoff et al. | 424/78.17 |
| 6,214,384 B1 | 4/2001 | Pallado et al. | |
| 6,224,630 B1 | 5/2001 | Bao et al. | 623/17 |
| 6,224,794 B1 | 5/2001 | Amsden et al. | 264/4.1 |
| 6,235,224 B1 | 5/2001 | Mathiowitz et al. | 264/4 |
| 6,238,403 B1 | 5/2001 | Greene, Jr. et al. | |
| 6,245,090 B1 | 6/2001 | Gilson et al. | |
| 6,251,661 B1 | 6/2001 | Urabe et al. | |
| 6,258,338 B1 | 7/2001 | Gray | 424/1.29 |
| 6,261,585 B1 | 7/2001 | Sefton et al. | 424/423 |
| 6,264,861 B1 | 7/2001 | Tavernier et al. | |
| 6,267,154 B1 | 7/2001 | Felicelli et al. | |
| 6,268,053 B1 | 7/2001 | Woiszwillo et al. | |
| 6,277,392 B1 | 8/2001 | Klein | |
| 6,280,457 B1 | 8/2001 | Wallace et al. | |
| 6,291,605 B1 | 9/2001 | Freeman et al. | 526/88 |
| 6,296,604 B1 | 10/2001 | Garibaldi et al. | |
| 6,296,622 B1 | 10/2001 | Kurz et al. | |
| 6,296,632 B1 | 10/2001 | Luscher et al. | |
| 6,306,418 B1 | 10/2001 | Bley | |
| 6,306,419 B1 | 10/2001 | Vachon et al. | |
| 6,306,425 B1 | 10/2001 | Tice et al. | |
| 6,306,427 B1 | 10/2001 | Annonier et al. | |
| 6,312,407 B1 | 11/2001 | Zadno-Azizi et al. | |
| 6,312,942 B1 | 11/2001 | Pluss-Wenzinger et al. | |
| 6,315,709 B1 | 11/2001 | Garibaldi et al. | 600/12 |
| 6,335,384 B1 | 1/2002 | Evans et al. | |
| 6,344,182 B1 | 2/2002 | Sutton et al. | |
| 6,355,275 B1 | 3/2002 | Klein | |
| 6,368,658 B1 | 4/2002 | Schwarz et al. | |
| 6,379,373 B1 | 4/2002 | Sawhney et al. | |
| 6,388,043 B1 | 5/2002 | Langer et al. | |
| 6,394,965 B1 | 5/2002 | Klein | |
| 6,423,332 B1 | 7/2002 | Huxel et al. | |
| 6,432,437 B1 | 8/2002 | Hubbard | |
| 6,436,112 B1 | 8/2002 | Wensel et al. | |
| 6,443,941 B1 | 9/2002 | Slepian et al. | |
| 6,458,296 B1 | 10/2002 | Heinzen et al. | |
| 6,476,069 B1 | 11/2002 | Krall et al. | |
| 6,495,155 B1 | 12/2002 | Tice et al. | |
| 6,544,503 B1 | 4/2003 | Vanderhoff et al. | |
| 6,545,097 B1 | 4/2003 | Pinchuk et al. | |
| 6,575,896 B1 | 6/2003 | Silverman et al. | |
| 6,602,261 B1 | 8/2003 | Greene, Jr. et al. | |
| 6,602,524 B1 | 8/2003 | Batich et al. | 424/489 |
| 6,605,111 B1 | 8/2003 | Bose et al. | |
| 6,629,947 B1 | 10/2003 | Sahatjian et al. | |
| 6,632,531 B1 | 10/2003 | Blankenship | |
| 6,652,883 B1 | 11/2003 | Goupil et al. | |
| 6,680,046 B1 | 1/2004 | Boschetti | 424/9.1 |
| 6,699,222 B1 | 3/2004 | Jones et al. | |
| 2001/0016210 A1 | 8/2001 | Mathiowitz et al. | |
| 2001/0036451 A1 | 11/2001 | Goupil et al. | 424/78.38 |

| | | | | | | |
|---|---|---|---|---|---|---|
| 2001/0051670 | A1 | 12/2001 | Goupil et al. ............... 523/113 | WO | WO 01/66016 | 9/2001 |
| 2002/0054912 | A1 | 5/2002 | Kim et al. | WO | WO 01/70291 A2 | 9/2001 |
| 2002/0061954 | A1 * | 5/2002 | Davis et al. ............... 524/474 | WO | WO 01/76845 | 10/2001 |
| 2002/0160109 | A1 | 10/2002 | Yeo et al. | WO | WO 01/93920 | 12/2001 |
| 2002/0182190 | A1 | 12/2002 | Naimark et al. | WO | WO 02/11696 A2 | 2/2002 |
| 2002/0197208 | A1 | 12/2002 | Ruys et al. | WO | WO 02/34298 | 5/2002 |
| 2003/0007928 | A1 | 1/2003 | Gray | WO | WO 02/34299 | 5/2002 |
| 2003/0032935 | A1 | 2/2003 | Damiano et al. | WO | WO 02/34300 | 5/2002 |
| 2003/0108614 | A1 | 6/2003 | Volkinsky et al. | WO | WO 02/43580 A2 | 6/2002 |
| 2003/0187320 | A1 | 10/2003 | Freyman | WO | WO 03/016364 | 2/2003 |
| 2003/0194390 | A1 | 10/2003 | Krall et al. | WO | WO03/051451 | 6/2003 |
| 2003/0206864 | A1 | 11/2003 | Mangin | WO | WO03/082359 | 9/2003 |
| 2004/0186377 | A1 | 9/2004 | Zhong et al. | WO | WO 2004/019999 | 3/2004 |
| 2005/0025800 | A1 | 2/2005 | Tan | WO | WO 04/073688 | 9/2004 |
| 2005/0037047 | A1 | 2/2005 | Song | WO | WO 2004/075989 | 9/2004 |

FOREIGN PATENT DOCUMENTS

| | | |
|---|---|---|
| EP | 0 243 165 | 10/1987 |
| EP | 0 294 206 | 12/1988 |
| EP | 0 402 031 | 5/1990 |
| EP | 0 422 258 | 4/1991 |
| EP | 0458745 A1 | 5/1991 |
| EP | 0458079 A2 | 11/1991 |
| EP | 0548079 A2 | 11/1991 |
| EP | 0 470 569 A1 | 2/1992 |
| EP | 0 547 530 B1 | 6/1993 |
| EP | 0 600 529 A | 12/1993 |
| EP | 0 623 012 B1 | 11/1994 |
| EP | 0 706 376 B1 | 4/1996 |
| EP | 0 730 847 A1 | 9/1996 |
| EP | 0 744 940 B1 | 12/1996 |
| EP | 0 797 988 A2 | 10/1997 |
| EP | 0067459 B | 10/1998 |
| EP | 0 764 047 | 8/2003 |
| EP | 0 993 337 | 4/2004 |
| ES | 2 096 521 | 3/1997 |
| JP | 59-196738 | 11/1884 |
| JP | 62-45637 | 2/1987 |
| JP | 4-74117 | 3/1992 |
| JP | 6-57012 | 3/1994 |
| JP | 9-110678 | 4/1997 |
| JP | 9-165328 | 6/1997 |
| JP | 9-316271 | 12/1997 |
| JP | 10-130329 | 5/1998 |
| JP | 2002 017848 | 1/2002 |
| NZ | 255409 | 2/1997 |
| NZ | 517377 | 8/2003 |
| WO | WO91/12823 | 5/1991 |
| WO | WO 92/21327 | 12/1992 |
| WO | WO 93/00063 | 1/1993 |
| WO | WO 93/19702 | 10/1993 |
| WO | WO 94/10936 | 5/1994 |
| WO | WO 95/03036 | 2/1995 |
| WO | WO 95/22318 | 8/1995 |
| WO | WO 95/33553 | 12/1995 |
| WO | WO 96/37165 | 11/1996 |
| WO | WO 96/39464 | 12/1996 |
| WO | WO 98/04616 | 2/1998 |
| WO | WO 98/10798 | 3/1998 |
| WO | WO 98/26737 | 6/1998 |
| WO | WO98/47532 | 10/1998 |
| WO | WO 99/00187 | 1/1999 |
| WO | WO 99/12577 | 3/1999 |
| WO | WO 99/43380 | 9/1999 |
| WO | WO 99/51278 | 10/1999 |
| WO | WO 99/57176 | 11/1999 |
| WO | WO 00/23054 | 4/2000 |
| WO | WO 00/40259 | 7/2000 |
| WO | WO 00/71196 | 11/2000 |
| WO | WO 00/74633 A2 | 12/2000 |
| WO | WO 01/12359 | 2/2001 |

OTHER PUBLICATIONS

Kerber et al., "Polyvinyl Alcohol Foam: Prepackaged Emboli for Therapeutic Embolization," *American Journal Roentgenol*, Jun. 1978, vol. 130, pp. 1193–1194.

Latchaw et al., "Polyvinyl Foam Embolization of Vascular and Neoplastic Lesions of the Head, Neck, and Spine," *Radiology*, Jun. 1979, 131, pp. 669–679.

Tadavarthy et al., "Polyvinyl Alcohol (Ivalon) as an Embolizing Agent," *The American Journal of Roentgenology Radium Therapy and Nuclear Medicine*, Nov., 1975, vol. 125, No. 3, pp. 609–616.

Tadavarthy et al., "Polyvinyl Alcohol (Ivalon) as an Embolizing Agent," *Seminars in Interventional Radiology*, vol. 1, No. 2, Department of Radiology, University of Minnesota Hospitals, Minneapolis, Minnesota, Jun. 1984, pp. 101–109.

Yusi et al., "submuscosal Injection of Polyvinyl Alcohol in Artificially Created Vesico–Ureteral Reflux: A Preliminary Report," Asian J. Surg. 18(2): 122–127 (Apr. 1995).

Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.* 17:541–548, Mar. 1996.

"Pulmonary artery pseudoaneurysm/aneurysm" Available Web Site: http://www.mamc.amedd.army.mil/williams/chest/vascular/paaneurysm/paaneyrysm.htm.

Bachtsi, A.R. et al., "An Experimental Investigation of Enzyme Release from Poly(vinyl alcohol) crosslinked Microspheres", *J. Microencapsulation*, vol. 12, No. 1, pp. 23–35; 1995.

Barr, J.D., et al., "Polyvinyl Alcohol Foam Particles Sizes and Concentrations Injectable through Microcatheters", *JVIR*, vol. 9, No. 1, pp. 113–118; 1998.

Barttinelli, L. et al., "New Class of Poly(vinyl alcohol) Polymrs as Column–Chromatography Stationary Phases for Candida Rugosa Lipase Isoforms Separation.", *J. Chromatogr A*, vol. 753, No. 1, pp. 47–55; 1996. Abstract. http://www.ncbi.nlm.nih.gov/entrez/query.fcgi?.

Berenstein, A. et al., "Catheter and Material Selection for Transarterial Embolization: Technical Considerations. II. Materials.", *Radiology*, vol. 132, No. 3, pp. 631–639; 1979.

Berenstein, A. et al., "Microembolization Techniques of Vascular Occlusion: Radiologic, Pathohologic, and Clinical Correlation", *AJNR AM I Neuroradiol*, vol. 2, No. 3, pp. 261–267; 1981. Abstract, http://www.ncbi.nlm.nih.gov/entrez/query.fcgi?.

Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578–1583 Available Web Site: http://www.hepatitis-central.com/hcv/hcc/embolization/references.html.

Buhle, Jr. EL, "Re: Re: Hepatic Arterial Embolization", *UCLA Medicine Online* Available Web Site: http://www.meds.com/archive/ve/mol-cancer/1996/msg00128.html.

Burczak, et al., "Long-term in vivo performance and biocompatibility of poly (vinyl alcohol) hydrogel macrocapsules for hybrid-type artificial pancreas", *Biomaterials*, vol. 17, No. 24, pp. 2351–2356, 1996, abs: http://www.ncbi.nlm.nih.gov/entrez/query.fcgi?cmd=retrieve&db=PubMed&list_uids=89824 . . . , pp. 1, 2002.

Burczak, et al., "Polymeric materials for biomedical purposes obtained by radiation methods. V. hybrid artificial pancreas", *Polim Med*, vol. 24, No. 1–2, pp. 45–55, 1994, abs: http://www.ncbi.nlm.nih.gov/entrez/query.fcgi?cmd=retrieve&db=PubMed&list_uids=7915 . . . , pp. 1, 2002.

Choe, et al., "An experimental study of embolic effect according to infusion rate and concentration of suspension in transarterial particulate embolization", *Invest Radiol*, vol. 32, No. 5, pp. 260–270, 1997, abs: http://www.ncbi.nlm.nih.gov/entrez/query.fcgi?cmd=retrieve&db=PubMed&list_uids=9140745&dopt+Abs . . . , pp. 1, 2002.

Clarian Health Methodist—Indiana Lions Gamma Knife Center, "Arteriovenous Malformation" Available Web Site: http://www.clarian.com/tyhealth/gammaknife/cond_arter.asp.

Colombo M, "Treatment of Hepatocellular Carcinoma", University of Milan, Inst Internal Med, Irccs Maggiore Res Unit Liver, Canc, Fire, Via Pace 9 1–20122 Milan, Italy Source: Journal of Viral Hepatitis, 1997;4:125–130 Available Web Site: http://home.texoma.net/~moreland/stats/hcc-9.html.

Derdeyn, et al., "Collagen-coated acrylic microspheres for embolotherapy: in vivo and in vitro characteristics", *American Journal of Neuroradiology*, vol. 18, No. 4, pp. 647–653, 1997, abs: http://www.ncbi.nlm.nih.gov/entrez/query.fcgi?cmd=retrieve&db=PubMed&list_uids=9127025&dopt=Abs . . . , pp. 1, 2002.

Derdeyn, et al., "Polyvinyl alcohol particle size and suspension characteristics", *American Journal of Neuroradiology*, vol.; 16, pp. 1335–1343, 1995.

DiLuccio et al., "Sustained-Release Oral Delivery of Theophylline by use of Polyvinyl Alcohol and Polyvinyl Alcohol-Methyl Acrylate Polymers", *Journal of Pharmaceutical Sciences*, Jan. 1994, vol. 83, No. 1, pp. 104–106.

Gander, et al., "Effect of polymeric network structure on drug release from cross-linked poly(vinyl alcohol) micromatrices", *Phar Res*, vol. 6, No. 7, pp. 578–584, 1989, abs: http://www.ncbi.nlm.nih.gov/entrez/query.fcgi?cmd=retrieve&db=PubMed&list_uids=25080 . . . , pp. 1, 2002.

Germano, et al., "Histopathological follow-up study of 66 cerebral arteriovenous malformations after therapeutic embolization with polyvinyl alcohol", *J Neurosurg*, vol. 76, No. 4, pp. 607–614, 1992, abs: http://www.ncbi.nlm.nih.gov/entrez/query.fcgi?cmd=retrieve&db=PubMed&list_uids=15452 . . . , pp. 1, 2002.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, Dec. 2000, vol. 11, No. 10, pp. 1244–1255.

Gohel, et al., "Formulation design and optimization of modified-release microspheres of diclofenac sodium", *Drug Dev Ind Pharm*, vol. 25, No. 2, pp. 247–251, 1999, abs: http://www.ncbi.nlm.nih.gov/entrez/query.fcgi?cmd=retrieve&db=PubMed&list_uids=10065360&dop=A . . . , pp. 1, 2002.

Goodwin, et al., "Overview of embolic agents and their indications", *Eleventh Annual International Symposium on Endovascular Therapy*, pp. 303–306, 1999.

Goodwin, et al., "Preliminary experience with uterine artery embolization for uterine fibroids", *Journal of Vascular and Interventional Radiology*, vol. 8, No. 4, pp. 517–526, 1997.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467–479, 1992, abs: http://www.ncbi.nlm.nih.gov/entrez/query.fcgi?cmd=retrieve&db=PubMed&list_uids=1601900&dopt=Abs . . . , pp. 1, 2002.

Hamada, et al., "Embolization with cellulose porous beads, II: Clinical Trial", abs: http://www.ajnr.org/content/abstract/17/10/1901?ijkey=R.a2vRMiet1Xw pp. 1–2, 200.

Horak, et al., "Hydrogels in endovascular embolization. I. Spherical particles of poly (2-hydroxyethyl methacrylate) and their medico-biological properties".

Horak, et al., "Hydrogels in endovascular embolization. II. Clinical use of spherical particles", *Biomaterials*, vol. 7, 1986.

Huang, et al., "Percutaneous endovascular embolization of intracerebral arteriovenous malformations. Experience in 72 cases", *Chin Med J*, vol. 108, No. 6, pp. 413–419, 1995, abs: http://www.ncbi.nlm.nih.gov/entrez/query.fcgi?cmd=retrieve&db=PubMed&list_uids=75552 . . . , pp. 1, 2002.

International Search Report for International Application No. PCT/US01/06981 (2 pages).

Jack, et al., "Radiolabeled polyvinyl alcohol particles: a potential agent to monitor embolization procedures", *Int J Rad Appl Instrum B*, vol. 13, No. 3, pp. 235–243, 1986, abs: http://www.ncbi.nlm.nih.gov/entrez/query.fcgi?cmd=retrieve&db=PubMed&list_uids=37712, pp. 1, 2002.

Joy C, et al., 1991, "Use of Preoperative Embolization in the Treatment of Vascular Metastatic Lesions of the Spine" Available Web Site: http://www.aaos.org/wordhtml/anmeet91/scipro/ppr472.htm.

Kai, et al., "The utility of the microcrystalline cellulose sphere as a particulate embolic agent: an experimental study", *American Journal of Radiology*, vol. 21, No. 6, pp. 1160–1163, 2000, or http://www.ajnr.org/cgi/content/full/21/6/1160, pp. 1–7, 2002.

Kan, et al., "In vivo microscopy of the liver after injection of lipiodol into the hepatic artery and portal vein in the rat", *Acta Radiologica*, vol. 30, pp. 419–425, 1989.

Kim, et al., "Composite poly(vinyl alcohol) beads for controlled drug delivery", *Pharm Res*, vol. 9, No. 1, pp. 10–16, 1992, abs: http://www.ncbi.nlm.nih.gov/entrez/query.fcgi?cmd=retrieve&db=PubMed&list_uids=1589392&dopt=Abs . . . , pp. 1, 2002.

Kurata, et al., "Preoperative embolization for meningiomas using PVA particles", *No Shinkei Geka,* vol. 20, No. 4, pp. 367–373, 1992, abs: http://www.ncbi.nlm.nih.gov/entrez/query.fcgi?cmd=retrieve&db=PubMed&list_uids=1570057&dopt=Abs . . . , pp. 1, 2002.

Kurosaki et al., "Evaluation of PVA–Gel Spheres as GI–Transit Controlling Oral Drug Delivery System", *Proceedings of the 19th International Symposium on Controlled Release of Bioactive Materials,* Jul. 26–31, 1992, Orlando, Florida, pp. 273–274.

Kusano, et al., "Low–dose particulate polyvinylalcohol embolization in massive small artery intestinal hemorrahage. Experimental and clinical results", *Invest Radiol,* vol. 22, No. 5, pp. 388–392, abs: http://www.ncbi.nlm.nih.gov/entrez/query.fcgi?cmd=retrieve&db=PubMed&list_uids=34963 . . . , pp. 1, 2002.

Labarre et al., "Complement activation by substitued polyacrylamide hydrogels for embolisation and implantation", *Biomaterials,* vol. 23, pp. 2319–2327, 2002.

Lammer, et al., "Transcatheteral embolization with polyvinyl alcohol—technic and experimental studies", *Rontgenblatter,* vol. 36, No. 1, pp. 10–14, 1983, abs: http://www.ncbi.nlm.nih.gov/entrez/ query.fcgi?cmd=retrieve&db=PubMed&list_uids=6823530&dopt+Abs . . . , pp. 1, 2002.

Leung et al., "Determinants of Postembolization Syndrome after Hepatic Chemoembolization", *Journal of Vascular and Interventional Radiology,* Mar. 2001, vol. 12, No. 3, pp. 320–326.

Markoff, et al., "Uterine arteriovenous malformation successfully embolized with a liquid polymer, isobutyl 2–cyanoacrylate", pp. 659–660, 1999.

Matsumaru, et al., "Embolic materials for endovascular treatment of cerebral lesions", *J Biomater Sci Poly Ed,* vol. 8, No. 7, pp. 555–569, 1997, abs: http://www.ncbi.nlm.nih.gov/entrez/ query.fcgi?cmd=retrieve&db=PubMed&list_uids=91953 . . . , pp. 1, 2002.

Mid–American Interventional Radiological Society, "New Treatment of Uterine Fibroids Avoids Surgery" Available Web Site: http://www.mirs.org/fibroids.htm.

Nakabayashi, et al., "Evaluation of particulate embolic materials with MR imaging, scanning electron microscopy, and phase–contrast microscopy", *American Journal of Neuroradiology,* vol. 18, No. 3, pp. 485–491, 1997, abs: http://www.ncbi.nlm.nih.gov/entrez/query.fcgi?cmd=retrieve&db=PubMed&list_uids=90904 . . . , pp. 1, 2002.

Nakstad, et al., "Embolization of intracranial arteriovenous malformations and fistulas with polyvinyl alcohol particles nad platinum fibre coils", *Neuroradiology,* vol. 34, No. 4, pp. 348–351, 1992, abs: http://www.ncbi.nlm.nih.gov/entrez/query.fcgi?cmd=retrieve&db=PubMed&list_uids=15284 . . . , pp. 1, 2002.

Nash, et al., "Modifications of polystyrenic matrices for the purification of proteins. II. Effect of the degree of glutaraldehyde–poly(vinyl alcohol) crosslinking on various dye ligand chromatography systems", *J Chromatogr A,* vol. 776, No. 1, pp. 55–63, 1997, abs:http://www.ncbi.nlm.nih.gov/entrez/ query.fcgi?cmd=retrieve&db=PubMed&list_uids=92860 . . . , pp. 1, 2002.

Nikishin LF et al., 1999, "Interventional radiology in diffuse toxic goiter", *European Congress of Radiology—ECR* 1999 Available Web Site: http://www.ecr.org/conferences/ecr1999/sciprg/abs/p090041.htm.

Ophir, et al., "Ultrasonic backscatter from contrast producing collagen microspheres", *Ultrasonic Imaging,* vol. 2, pp. 67–77, 1980.

Oregon Health Sciences University, "Fibroid Embolization" Available Web Site: http://www.uhmc.edu/dotter–fibroid.

Parker, et al., "A particulate contrast agent with potential for ultrasound imaging of liver", *Ultrasound in Medicine and biology,* vol. 13, No. 9, pp. 555–566, 1987.

Pesant A.C. et al., 1997, "Dural fistulas involving the cavernous sinus: Treatment by embolization—7 cases", *European Congress of Radiology—ECR* 1997 Available Web Site: http://www.ecr.org/conferences/ecr1997/sciprg/abs/9703088p.htm.

Physicians' Desk Reference Family Guide to Women's Health, "Chapter 7—Common Disorders of the Reproductive System" Available Web Site: http://www.healthsquare.com/pdrfg/wh/chapters/wh1ch01.htm.

Pritchard, et al., "*Poly(Vinyl Alcohol*): Basic Properties and Uses, ",London, England: Gordon and Breach Science Publishers.

Pryor J and Berenstein A., "Epistaxis (Nose–bleeds)" Available Web Site: http://www.wehealny.org/inn/Radiology/nosebleeds.html.

Purdy, et al., "Arteriovenous malformations of the brain: choosing embolic materials to enhance safety and ease of excision", *J Neurosurg,* vol. 77, No. 2, pp. 217–222, 1992, abs: http://www.ncbi.nlm.nih.gov/entrez/ query.fcgi?cmd=retrieve&db=PubMed&list_uids=16250 . . . , pp. 1, 2002.

Quisling, et al., "Histopathology analysis of intraarterial polyvinyl alcohol microemboli in rat cerebral cortex", *American Journal of Neuroradiology,* vol. 5, pp. 101–104, 1984.

Rajan et al., "Sarcomas Metastatic to the Liver: Response and Survial after Cisplatin, Doxorubicin, Mitomycin–C, Ethiodol, and Polyvinyl Alcohol Chemoembolization", *Journal of Vascular and Interventional Radiology,* Feb. 2001, vol. 12, No. 2, pp. 187–193.

Ramos, et al., "Tumor vascular signals in renal masses: detection with Doppler US", *Radiology,* vol. 168, No. 3, pp. 633–637, 1988.

Shafik, A., "Intraesophageal Polytef injection for the treatment of reflux esophagitis", *Department of Surgery and Experimental Research, Faculty of Medicine, Cairo University,* Cairo, Egypt, pp. 1–2, Received: Jun. 22, 1994; Accepted: Oct. 15, 1994 http://www.ahmedshafik.org/Group–D/d016.htm.

Spickler et al., "The MR appearance of endovascular embolic agents in vitro with clinical correlation", *Comput Med Imaging Graph,* vol. 14, No. 6, pp. 415–423, 1990, abs: http://www.ncbi.nlm.nih.gov/entrez/ query.fcgi?cmd=retrieve&db=PubMed&list_uids=21487 . . . , pp. 1, 2002.

Spies JB, "Georgetown University Medical Center. Uterine Fibroid Embolization (UFE). An alternative to surgery for patients with uterine fibroids. Literature Review." Available Web Site: http://www.dml.georgetown.edu/fibroids.

Strunk, et al., "Treatment of cogenital coronary arteriovenous malformations with microparticle embolization", *Cathet Cardiovasc Diagn,* vol. 22, No. 2, pp. 133–136, 1991, abs: http://www.ncbi.nlm.nih.gov/entrez/query.fcgi?cmd=retrieve&db=PubMed&list_uids=2009563&dopt=Abs . . . , pp. 1, 2002.

Swanson DA et al., 1980, "The role of embolization and nephrectomy in the treatment of metastatic renal carcinoma", Urologic Clinics of North America 7(3):719–730, 1980. University of Pennsylvania Cancer Center—Oncolink. Available Web Site; http://www.oncolink.upenn.edu/pdg_html/cites/00/00585.html.

Tabata et al., "Tumor accumulation of poly(vinyl alcohol) of different sizes after intravenous injection", *Journal of Controlled Release*, Jan. 2, 1998, vol. 50, Nos. 1–3, pp. 123–133.

Tao, et al., "Study of microspheres for embolization of the hepatic artery", *Yao Xue Bao*, vol. 23, No. 1, pp. 55–60, 1988, abs: http://www.ncbi.nlm.nih.gov/entrez/ query.fcgi?cmd=retrieve&db=PubMed&list_uids= 3400477&dopt=A, pp. 1, 2002.

Tao, et al., "Study on embolization of hepatitic artery using microspheres", Acta Pharmaceutica Sinica vol. 23, No. 1, pp. 55–60; 1988. Translation.

Terada, et al., "Preoperative embolization of meningiomas fed by ophthalmic branch arteries", *Surg Neurol*, vol. 45, No. 2, pp. 161–166, abs: http://www.ncbi.nlm.nih.gov/entrez/ query.fcgi?cmd=retrieve&db=PubMed&list_uids= 86070 . . . , pp. 1, 2002.

Thanoo, et al., "Controlled release of oral drugs from cross–linked polyvinyl alcohol microspheres", J *Pharm Pharmcol*, vol. 45, No. 1, pp. 16–20, 1993, abs: http://www.ncbi.nlm.nih.gov/entrez/ query.fcgi?cmd= retrieve&db=PubMed&list_uids=8094438&dopt=Abs . . . , pp. 1, 2002.

Thanoo, et al., "Tantalum loaded silicone microspheres as particulate emboli", *J Microencapsul*, vol. 8, No. 1, pp. 95–101, 1991, abs: http://www.ncbi.nlm.nih.gov/entrez/ query.fcgi?cmd=retrieve&db=PubMed&list_uids= 1880697&dopt=Abs . . . , pp. 1, 2002.

The Fibroid Embolization Center of the New York United Hospital Medical Center, "Fibroid Facts" Available Web Site: http://www.uhmc.com/fibro2.htm.

The Vanderbilt–Ingram Cancer Center, "Kidney Cancer." Availabel Web Site: http://www.mc.Vanderbilt.Edu/cancer/cancerinfgo/kidney.html.

Tikkakoski, et al., "Preoperative embolization in the management of neck paragangliomas", *Laryngoscope*, vol. 107, pp. 821–826, 1997.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148–156. 1994, abs:http://www.ncbi.nlm.nih.gov/entrez/ query.fcgi?cmd=retrieve&db=PubMed&list_uids= 80912 . . . , pp. 1, 2002.

UCLA Medical Group, "Uterine Embolziation—Introduction—Statistics—Preservation of Fertility." Available Web Site: http://www.fibroids.org.

UCLA Radiological Sciences, "A summary of terms appearing in this text." Available Web Site: http://www.radsci.ucal.edu:8000/aneurysm/terms.html.

University Medical Center SUNY Stony Brook, Department of Urology, "Variococele and its treatment." Available Web Site: http://www.hsc.sunysb.edu/urology/male_inf...variocoele_and _it_treatment.html.

Vivas S et al., "Arterioportal fistula and hemobilia in a patient with hepatic transplant", Gastroenterol Hepatol, 1998, Feb.;21(2):88–9 Available Web Site: http://www.doyma.es/copiani/revistas/gastro/abstr/absp080.html.

Vogel F, "Nonsurgical Management of Uterine Fibroids" Available Web Site: http://www.holyname.org/brochure/fibroids.html.

Wakhloo, et al. "Extended preoperative polyvinyl alcohol microembolization of intracranial meningiomas: Assessment of two embolization techniques", *American Journal of Neuroradiology*, vol. 14, pp. 571–582, 1993.

Walker WJ, "Non Surgical Treatment of Fibroids in the UK by Uterine Artery Embolisation—An Alternative to Hysterectomy, Myomectomy and Myolysis" Available Web Site: http://www.fibroids.co.uk/thepaper.html.

Walsh RM et al., 1998, "Role of Angiography and Embolization for Acute Massive Upper Gastrointestinal Hemorrhage." Department of General Surgery and Radiology, Cleveland Clinic Foundation, Cleveland, Ohio. Available Web Site: http://www.ssat.com/98ddw/abstscoort–47.html Wikholm G et al., 1996, "Embolization of Cerebral Arteriovenous Malformations: Part I—Techniques, Morphology and Complications", Departments of Neurology (CL) and Interventional Radiology (GW, PS), Sahlgrenska University Hospital, Goteborg, Sweden. Neurosurgery. 1996, Sep.;39(3):448–57; discussion 457–9. Available Web Site: http://www.wwilkins.com/neurosurgery/ 0148–396X9–96inter.html.

Worthington–Kirsch RL, 1999, "Interventionalists offer management option for uterine fibroids." Diagnostic Imaging, pp. 47–49. Available Web Site: http://www.dimag.com/references/9903wortrefs.html.

Worthington–Kirsch, et al., "Uterine arterial embolization for the management of leiomyomas: Quality–of–life assessment and clinical response", *Radiology*, vol. 208, No. 3, 625–629, 1998.

Yamada, et al., "Extended intraarterial cisplatin infusion for treatment of gynecological cancer after alteration of intrapelvic blood flow and implantation of a vascular access device", *International Radiology*.

Bourke et al., "Protein Drug Release from Photocrosslinked Poly(vinyl alcohol) Hydrogels,"*Society for Biomaterials 28th Annual Meeting Transactions*, p. 144 (2002).

Capozza et al., "Endoscopic treatment of vesico–ureteric reflux and urinary incontinence: technical problems in the paediatric patients,"*British Journal of Urology*, 75(4):538–542 (Apr. 1995).

Cruise et al., "*In Vitro and In Vivo*Characterization of a Hydrogel–Based Aneurysm Embolization System,"*Society for Biomaterials 28th Annual Meeting Transactions*, p. 203 (2002).

Duckwiler et al., "Catheters, embolic agents spark neurointervention,"*Diagnostic Imaging*, 16(5):66–72 (May 1994).

Ersek et al., "Bioplastique: A New Textured Copolymer Microparticle Promises Permanence in Soft–Tissue Augmentation,"*Plastic and Reconstructive Surgery*, 87(4):693–702 (Apr. 1991).

Eskridge, "International Neuroradiology,"*Radiology*, 172:991–1006 (Nov. 1989).

Gramiak et al., "Echocardiography of the Arctic Root," *Investigative Radiology*, 3(5):356–366 (Sep.–Oct. 1968).

Gupta et al., "Plasma–induced graft polymerization of acrylic acid onto poly(ethylene terephthalate) films: characterization and human smooth muscle cell growth on grafted films,"*Biomaterials*, 23:863–871 (2002).

Halstenberg et al., "Biologically Engineered Protein–graft–Poly(ethylene glycol) Hydrogels: A Cell Adhesive and Plasmin–Degradable Biosynthetic Material for Tissue Repair," *Biomacromolecules*, 3(4):710–723 (2002).

Hirano et al., "Transcutaneous Intrafold Injection for Unilateral Vocal Fold Paralysis: Functional Results,"*Ann Otol. Rhinol Laryngol.*, 99(8):598–604 (Aug. 1990).

Jung et al., "Sulfobutylated poly(vinyl alcohol)–graft–poly-(lactide–co–glycolide)s facilitate the preparation of small negatively charged biodegradable nanospheres,"*Journal of Controlled Release*, 67:157–169 (2000).

Khankan et al., "Embolic Effects of Superabsorbent Polymer Microspheres in Rabbit Renal Model: Comparison with Tris–acryl Gelatin Microspheres and Polyvinyl alcohol,"*Radiation Medicine*, 22(6):384–390 (2004).

Kim et al., "Poly(vinyl alcohol) beads with core–shell structure for drug delivery,"*Cosmetic and Pharmaceutical Applications of Polymers*, Plenum Press, New York, pp. 209–214 (1991).

Kim et al., "Suspension polymerized poly(vinyl alcohol) beads for drug delivery,"*Polymeric Materials: Science and Engineering, Proceedings of the ACS Division of Polymeric Materials: Science and Engineering*, 63:64–67 (1990).

Krinick et al., "A polymeric drug delivery system for the simultaneous delivery drugs activatable by enzymes and/or light", *J. Biomater. Sci. Polymer Edn*, 5(4):33–324 (1994).

Laurent, "Materials and biomaterials for interventional radiology,"*Biomed & Pharmacother.*, 52:76–88 (1998).

Lemperle et al., "PMMA Microspheres for Intradermal Implantation: Part I. Animal Research,"*Annals of Plastic Surgery*, 26(1):56–63 (Jan. 1991).

Levy et al., "Transcather Uterine Artery Embolization for the Treatment of Symptomatic Uterine Fibroid Tumors," *Journal of Women's Imaging*, 2(4):168–175 (2000).

Lipman, "Uterine artery embolization for the treatment of symptomatic uterine fibroids: A review,"*Applied Radiology*, 29(7):15–20 (Jul. 2000).

Maruhashi, "Modified Polyvinyl Alcohols I and II,"*Polyvinyl Alcohol –Developments*, John Wiley & Sons, Chichester, England, pp. 160–161 and pp. 186–191.

Namiki, "Application of Teflon Paste for Urinary Incontinence –Report of 2 Cases,"*Uro. Int.*, 39:280–282 (1984).

Orienti et al., "Crosslinked Polyvinylalcohol Hydrogels as Vehicles for Hydrophilic Drugs,"*Arch. Pharm. Med. Chem.*, 333:421–424 (2000).

Pedley et al., "Hydrogels in Biomedical Applications,"*British Polymer Journal*, 12:99–110 (Sep. 1980).

Pistel et al., "Brush–like branched biodegradable polyesters, part III Protein release from microsphres of poly(vinyl alcohol)–graft–poly(D,L–lactic–co–glycolic acid),"*Journal of Controlled Release*, 73:7–20 (2001).

Politano et al., "Periurethral Teflon Injection for Urinary Incontinence," *The Journal of Urology*, 111:180–183 (1974).

Progelhof et al. "Table 4.21. Properties of eletrical insulating films (101),"*Polymer Engineering Principles: Properties, Processes, and Tests for Design*, Hanser Publsishers, Munich, p. 383 (1993).

PVA Plus, AngioDynamics™Inc., "Reliable PVA Foam Formulated for Consistency and Controlled Delivery–Embolization Particles Ordering Information," www. angiodynamics.com, 2 pages (Aug. 2002).

Rhine et al., "Polymers for Sustained Macromolecule Release: Procedures to Fabricate Reproducible Delivery Systems and Control Release Kinetics,"*Journal of Pharmaceutical Sciences*, 69(3):265–270 (Mar. 1980).

Schetky, "Shape–Memory Alloys,"*Encyclopedia of Chemical Technology*, Third Edition, vol. 20, John Wiley & Sons, New York, pp. 726–736 (1982).

Shafik, "Intraesophageal Polytef injection for the treatment of reflux esophagitis,"*Surg. Endosc.*, 10:329–331 (1996).

Siskin et al., "Pathologic Evaluation of a Spherical Polyvinyl Alcohol Embolic Agent in a Porcine Renal Model,"*J. Vasc. Interv. Radiol.*, 14:89–98 (2003).

Smith et al., "Evaluation of Polydimethylsiloxane as an alternative in the Endoscopic Treatment of Vesicoureteral Reflux,"*The Journal of Urology*, 152:1221–1224 (Oct. 1994).

Soppimath et al., "Controlled release of antihypertensive drug from the interpenetrating network poly(vinyl alcohol)–guar gum hydrogel microspheres,"*J. Biomater. Sci. Polymer Edn*, 11(1):27–43 (2000).

Strasnick et al., "Transcutaneous Teflon™Injection for Unilateral Vocal Cord Paralysis: An Update,"*The Laryngoscope*, 101:785–787 (Jul. 1991).

Stridbeck, H. et al., "Collateral Circulation Following Repeated Distal Embolization of the Hepatic Artery in Pigs,"*Invest. Radiol.*, 19(3): 179–183 (1984).

Tian et al., "Design and synthesis of amphiphilic poly (ethylene glycol) derivatives as micellar drug delivery systems,"*Polymer Preprints*, 43(2):719–720 (Fall 2002).

Winters et al., "Periurethral injection of collagen in the treatment of intrinsic sphincteric deficiency in the female patient,"*The Urologic Clinics of North America*, 22(3):673–678 (Aug. 1995).

Wright, K.C. et al., "Partial Splenic Embolizatioin Using Polyvinyl Alcohol Foam, Dextran, Polystyrene, or Silicone," *Radiology*, 142:351–354, Feb. 1982.

Yoon et al., "Surface Immobilization of Galactose onto Aliphatic Biodegradable Polymers for Hepatocyte Culture," *Biotechnol. Bioeng.*, 78(1):1–10 (Apr. 5, 2002).

Zisch et al., "Covalently conjugated VEGF–fibrin matrices for endothelialization,"*Journal of Controlled Release*, 72:101–113 (2001).

Kim et al., "Hollow Silica Spheres of Controlled Size and Porosity by Sol–Gel Processing", J. Am. Ceram. Soc., 74(8): 1987–1992 (Aug. 1991).

Abbara, S. et al. "Transcervical Expulsion of a Fibroid as a Result of Uterine Artery Embolization for Leiomyomata", *JVIR*, vol. 10, No. 4, pp. 409–411; 1999.

Abrahams, J.M. et al., "Topic Review: Surface Modifications Enhancing Biological Activity of Guglielmi Detachable Coils in Treating Intracranial Anurysms", *Surg. Neurol.*54:34–41, 2000.

Abrahams, J.M. et al. "Delivery of Human Vascular Endothelial Growth Factor with Platinum oils Enhances Wall Thickening and Coil Impregnation in a Rat Aneurysm Model", *AJNR Am. J. Neuroradiol.*22:1410–1417, Aug. 2001.

Ahuja, A.A. "Platinum Coli Coatings to Increase Thromogenicity: A Preliminary Study in Rabbits", *AJNR Am. J. Neuroradiol.*14:794–798; Jul./Aug. 1993.

Antibody Labeling http://www.altcorp.com/AffinityLabeiling/ablaeling.htm, pp. 1–6, May 20, 2003.

Berkowitz, R.P. et al., "Vaginal Expulsion of Submucosal Fibroids After Uterine Artery Embolization", *Journal of Reproductive Medicine*, vol. 44, No. 4, pp. 373–376; Apr. 1999 http://www.reproductivemedicine.com.

Bradley, E.A. et al., "Transcatheter Uterine Embolisation to Treat Large Uterine Fibroids", *British Journal of Obstetrics and Gynaecology*, vol. 105, pp. 235–240; Feb. 1998.

Brockmann, J. et al., "Radiolabeling of p–Bz–DOTA–CD–11c antibody with ∞∞Y: Conjugation, Labeling, Biodistribution studies", 2 pages, 2000 http://ww.kernchemie.uni–mainz.de/downloads/jb2000/b14 brockmann.pdf.

Carrll, B.A. et al., "Microbubbles as Ultrasonic Contrast Agents", *Investigative Radiology*, vol. 14, No. 3, Supplement to May–Jun. 1979.

Carroll, B.A. et al., "Gelatin Encapsulated Nitrogen Microbubbles as Ultrasonic Constrast Agents", *Journal of Clinical and Laboratory Research*, vol. 15, No. 1; Feb. 1980.

Carstensen, E.L. et al., "Determination of the Acoustic Properties of Blood and its Components", *Journal of Acoustical Society of America*, vol. 25, No. 2; Mar. 1953.

Cirkel, U. et al., "Experience with Leuprorelin Acetate Depot in the Treatment of Fibroids: A German Multicentre Study", *Clinical Therapeutics*, vol. 14, Suppl. A, 1992.

Deasy, P. B., "*Microencapsulation and Related Drug Processes*", New York, NY, Marcel Dekker, Inc., 345 pages, 1984 (Table of Contents only).

DeGast, A.N. et al., "Transforming Growth Factor β–0coated Platinum Coils for Endovascular Treatment of Aneursyms: An Animal Study", *Neurosurgery*, vol. 49, No. 3, pp. 690–696, Sep. 2001.

* cited by examiner

PROCESSES FOR MANUFACTURING POLYMERIC MICROSPHERES

TECHNICAL FIELD

This invention generally relates to polymeric microspheres and processes of manufacturing polymeric microspheres.

BACKGROUND INFORMATION

Microparticles, microcapsules and microspheres have important applications in the medical, pharmaceutical, agricultural, textile and cosmetics industries as delivery vehicles, cell culture substrates or as embolization agents.

Polymeric microspheres, i.e., microspheres formed (at least in part) from a crosslinkable polymer, have found a variety of uses in the medical and industrial areas. They may be employed, for example, as drug delivery agents, tissue bulking agents, tissue engineering agents, and embolization agents. Accordingly, there are numerous methods directed toward preparing polymeric microspheres. These methods include dispersion polymerization of the monomer, potentiometric dispersion of a dissolved crosslinkable polymer within an emulsifying solution followed by solvent evaporation, electrostatically controlled extrusion, and injection of a dissolved crosslinkable polymer into an emulsifying solution through a porous membrane followed by solvent evaporation.

Additional methods include vibratory excitation of a laminar jet of monomeric material flowing in a continuous liquid medium containing a suitable suspending agent, irradiation of slowly thawing frozen monomer drops, and continuous injection of a dissolved crosslinkable polymer into a flowing non-solvent through a needle oriented in parallel to the direction of flow of the non-solvent.

These methods known in the art have shortcomings that may curtail the formation of uniformly sized microspheres of small diameter ranges (e.g., in the range of 100–600 microns) for various applications, particularly when the base material has a high viscosity.

SUMMARY OF THE INVENTION

The present invention facilitates production of small, uniformly sized polymeric microspheres in a manner not limited, in terms of obtainable size range, by the viscosity or density of the structural polymer.

In one aspect, a process of the invention includes generating spherical beads or particles of a desired or predetermined size from a suitable template polymer, contacting the beads or particles with a structural polymer, such as polyvinyl alcohol, and crosslinking the structural polymer into the beads or particles. The template polymeric material may subsequently be removed, resulting in polymeric microspheres.

As used herein, the term "template" polymer refers to a soluble polymer that is used to create temporary particle forms (i.e., beads), which may be porous or non-porous depending on the template polymer that is selected. A "structural" polymer invades or surrounds the temporary form and, following crosslinking, creates the permanent structure of the particle. Structural polymers are generally chemically crosslinkable, i.e., crosslink through the formation of covalent bonds. Chemically crosslinkable polymers may be crosslinked through, for example, photoinitiation or other application of actinic radiation, by exposure to a chemical crosslinking agent or thermal energy or through freeze-thaw cycles.

In a preferred embodiment, a process of the invention includes generating spherical beads of a desired size from a starting material including a porous template polymer and a solvent; diffusing the structural polymer into the beads; and crosslinking at least the structural polymer. The solidified template polymer may exhibit a porosity gradient, from the outside to the inside of the beads, which determines the manner and extent to which the structural polymer diffuses into the beads. Alternatively, the template may have homogeneous porosity. The template polymer is subsequently removed, leaving behind a microsphere composed of only the structural polymer. In this way, the process of the invention overcomes the problem associated with generation of smaller-sized polymeric microspheres from viscous polymer solutions, by starting with particles of a desired size and subsequently contacting the particles with a structural polymer.

In an alternative embodiment of the diffusion method, spherical beads of a desired size are generated from starting material including a template polymer and a crosslinking agent. The structural polymer is diffused into the beads. The inclusion of a crosslinking agent in the starting material causes the structural polymer to crosslink into the beads upon contact therewith. The template polymer is subsequently removed, resulting in the formation of polymeric microspheres.

In another preferred embodiment, a process of the invention includes generating spherical particles or beads of a desired predetermined size from a starting material including a generally non-porous template polymer, such as methyacrylate, and contacting the beads with a structural polymer. To prevent premature damage to the beads, the template polymer in this case should not dissolve in the carrier of the structural polymer. The latter polymer is subsequently crosslinked and the template polymeric material is removed, leaving behind intact hollow polymeric spherical particles. In this embodiment the beads are coated on the outside surface with a generally uniform layer of the structural polymer, as opposed to the structural polymer diffusing within the beads. The beads can be either soaked in a solution containing the structural polymer, or the structural polymer can be sprayed or otherwise applied onto the outer surfaces of the beads. The structural polymer can be crosslinked, whether diffused within or applied onto the outer surface of the particles or beads, by a chemical crosslinking agent such as formaldehyde or glutaraldehyde, or by exposure to actinic or thermal energy.

The size of the beads can be determined or influenced by passing the mixture including a template polymer through a droplet generator with a nozzle adapted to generate droplets of a predetermined size, and subsequently depositing the droplets into a gelling solution to solidify the droplets, resulting in spherical beads. The size distribution of the beads can be improved by sieving.

Alternatively, a generally non-porous template polymer, such as methacrylate, can be used for generation of beads using spheronization technology known in the art.

In a preferred embodiment of the invention, a desired size for the resulting polymeric microspheres is in the range 1–50 microns diameter. Other desirable size ranges for the polymeric microspheres include microspheres in the size range 50–100 microns diameter, microspheres in the size range 100–600 microns diameter and microspheres in the size range 600–1000 microns diameter.

The foregoing and other objects, aspects, features and advantages of the invention will become more apparent from the following description and from the claims.

BRIEF DESCRIPTION OF THE DRAWINGS

The foregoing and other objects of the invention and the various features thereof may be more fully understood from the following description when read together with the accompanying illustrative flowcharts in which like reference characters generally refer to the same parts throughout the different illustrations.

DETAILED DESCRIPTION OF THE INVENTION

The methods of the invention facilitate the generation of polymeric microspheres of size ranges smaller than 600 microns diameter by forming template beads or particles of a predetermined size and subsequently contacting the beads with a structural polymer. Polymeric microspheres of size ranges smaller than 600 microns can be generated by diffusing a structural polymer, such as polyvinyl alcohol, within spherical beads of a predetermined size made from a starting material including a template polymer such as alginate, chitosan, etc. Diffusion of the structural polymer into the beads can be achieved by, for example, soaking the beads in a solution of the structural polymer. The porous nature of the beads favors the diffusion of the polymer into the beads. Alternatively, this process may be carried out under conditions that enhance diffusion, e.g., the addition of a surfactant, elevated temperature and/or pressure.

Polymeric microspheres of size ranges smaller than 600 microns diameter can also be generated by coating the outer surface of prefabricated beads or particles made from a template polymer, such as methacrylate, with a structural polymer. In this case, the beads are generally non-porous in morphology and receive a substantially even coating of the structural polymer either by, for example, soaking the beads in a solution or suspension of a structural polymer or by spraying the outer surface of the beads with such a solution or suspension.

Figure 1:
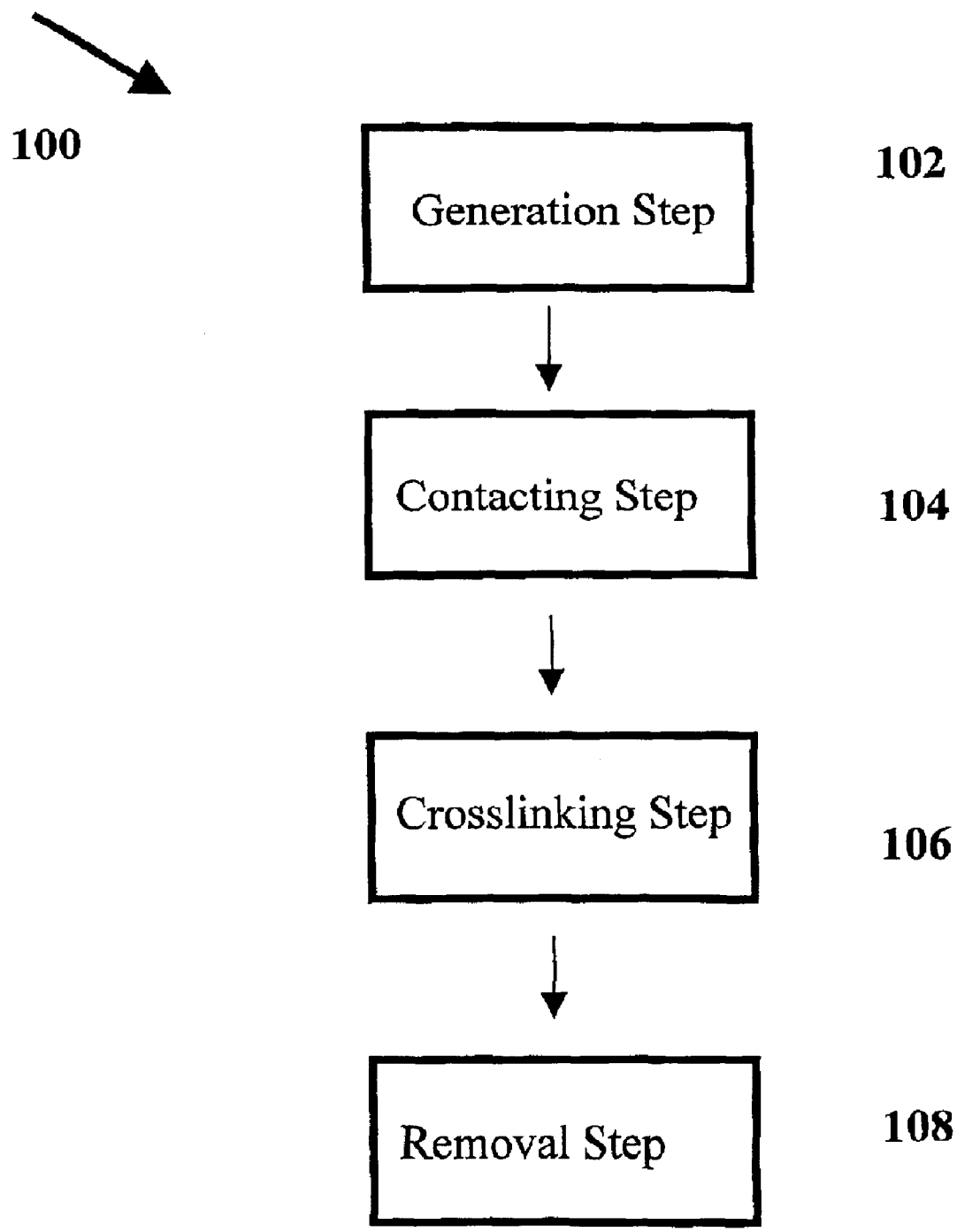
FIG. 1 is an illustrative flow diagram depicting the basic steps involved in a process of the invention.

FIG. 1 shows a flow chart 100 illustrating the basic steps involved in a process of the invention. The prefabrication or generation step 102 includes formation of spherical beads or particles of a predetermined size from a starting material containing a template polymer. In one embodiment, the starting material includes a template polymer and a solvent.

In general, the role of the template polymer is to act as a removable carrier to encapsulate or support the structural polymer, which is introduced in a subsequent step. Accordingly, the template polymer will be soluble in a solvent that does not attack the crosslinked structural polymer, and may be, for example, an ionically crosslinkable material. Omission of the structural polymer at this stage enables the formation of uniformly sized spherical beads of small size ranges, preferably smaller than 600 microns diameter.

Suitable porous template polymers include, for example, alginates, polysaccharides, carrageenans, chitosan, hyaluronic acid, or other ionically crosslinkable polymers (also known as "shape-forming agents"), such as the classes of carboxylic-, sulfate-, or amine-functionalized polymers. The template polymer can also be generated from a blend of one or more of the above synthetic or naturally occurring materials, or derivatives thereof. In one preferred embodiment of the invention, the template polymer is an alginate, which is ionically crosslinkable.

The solvent utilized in a process of the invention is chosen based on several considerations. Firstly, the solvent should be easily removable by evaporation, and should therefore have a relatively low boiling point. The solvent should be capable of dissolving the starting material without interfering with the structural polymer crosslinking. Absence of any environmental contaminants and ease of disposal are also worthwhile criteria in the selection of the solvent. Deionized water and saline solution are preferred as solvents; however, solvents can also be selected from polar and nonpolar laboratory solvents, such as, for example, acetone, methane and ethanol (which are polar), or hexane and benzene (nonpolar).

The generation step 102 is followed by the contacting step 104, which involves contacting the prefabricated spherical beads or particles with a structural polymer. The crosslinking step 106 involves crosslinking the structural polymer into the beads or particles. The last step 108, involves the removal of the template polymer from the beads, resulting in the formation of polymeric microspheres. The template polymer is removed by soaking the beads in a suitable solvent.

The structural polymer utilized in the contacting step 104 can be selected from a wide variety of generally chemically crosslinkable polymers such as, for example, vinyl polymers, polyacrylamides, polyethylene glycol, polyamides, polyureas, polyurethranes, polyvinyl alcohols, and derivatives thereof. For some (e.g., embolic) applications, a hydrophilic polymer, such as polyvinyl alcohol, will be preferred.

The structural polymer is subsequently crosslinked in step 106 by a crosslinking agent. The crosslinking agent can be a chemical agent such as, for example, formaldehyde or glutaraldehyde, or the like thereof. The structural polymer can also be crosslinked by application of photoinitiation, an ionic agent or actinic radiation such as, for example, ultraviolet or gamma radiation, or an electron beam.

The porosity of the outer polymeric shell can be controlled by the addition to the polymeric solution of a filler agent, such as starch, that is not crosslinked in the crosslinking step and can be removed easily by rinsing the beads.

The size of the polymeric particles depends on the method used for generating the spherical beads. Several techniques can be utilized for the generation of spherical particles or beads from a suitable starting material. A droplet generator can produce spherical droplets of a predetermined diameter by forcing a jet stream of a solution containing a template polymer and a solvent through a nozzle, which is subjected to a periodic disturbance to break up the laminar jet stream into droplets. This may involve the use of a nozzle having, for example, an electrostatic or piezoelectric element. The size of the droplets depends on the frequency at which the element is driven. The uniformly sized droplets fall into a solution containing a positively or a negatively charged agent, such as calcium or barium, or a charged polymer, such as polyacrylic acid, resulting in the conversion of the liquid droplets into solid beads.

The manner in which liquid droplets are solidified affects the properties of the particles. $Ca^{2+}$, for example, is a strong gelling ion, so a high concentration of, for example, $CaCl_2$ will create an inwardly moving gelling zone as the droplet solidifies. This creates a high porosity gradient, with the solidified particle exhibiting a smooth exterior with minimal porosity (e.g., microporous with an average pore size of 10 microns or less) and increasing porosity (e.g., up to about 50 microns) at the particle core. By adding non-gelling ions (e.g., $Na^+$ in the form of NaCl) to the solution in order to compete with the gelling ions, it is possible to limit the porosity gradient, resulting in a more uniform intermediate porosity throughout the particle. The porosity of the particle, in turn, affects the distribution of the structural polymer. A higher porosity gradient will result in concentration of the structural polymer on the surface of the particle and, following removal of the template polymer, a relatively hollow sphere. A lower porosity gradient, by contrast, will result in a more even distribution of the structural polymer throughout the particle, and a more densely crosslinked finished sphere.

In an alternative embodiment, beads are generated from a mixture of a template polymer and a crosslinking agent, such as formaldehyde or glutaraldehyde. The beads are contacted with a structural polymer and the template polymer is subsequently removed, resulting in the formation of polymeric spherical particles. Thus, by inclusion of a crosslinking agent in the starting material for generating the beads, this embodiment eliminates the need for a discrete crosslinking step 106.

Figure 2:
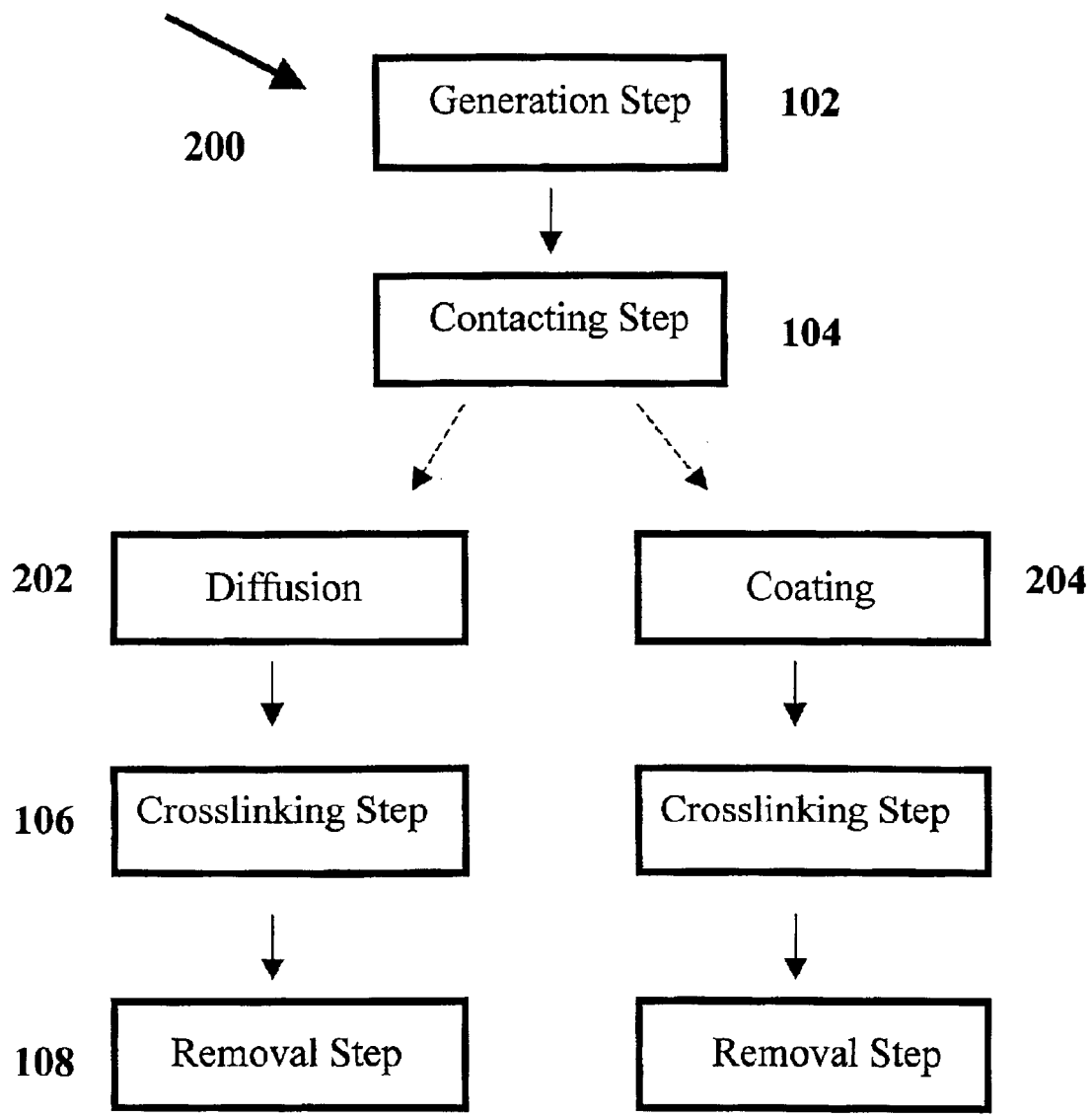
FIG. 2 is an illustrative flow diagram representing the steps involved in a process of the invention, where the contacting step is carried out by either diffusion or coating.

FIG. 2 shows a flow chart 200 illustrating the various steps in particular embodiments of the invention, where the contacting step 104 includes diffusion 202 or coating 204. The contacting step employing diffusion 202 is based on diffusing the structural polymer into the prefabricated beads, generated from a starting material including a template polymer and a solvent. Diffusion can be achieved by, for example, soaking the beads in a solution of the structural polymer.

The contacting step employing coating 204 is based on application of a uniform layer of the structural polymer on the outer surface of the beads. The structural polymer can be applied by, for example, spraying the polymer on the surfaces of prefabricated beads made from a generally non-porous template polymer, such as methyacrylate, or soaking such beads in a solution of a structural polymer. An even spray-coating of the microspheres can be achieved by, for example, suspending the beads in air while spraying.

The structural polymer is crosslinked into the beads in step 106. The template polymer, which generally comprises a porous polymer in the diffusion embodiment 202, and a non-porous polymer in the coating embodiment 204, is subsequently removed in step 108. The end product is microspheres of a desired predetermined size and composed of the structural polymer. Ionically crosslinkable materials, such as, for example, shape-forming agents are dissolved using suitable solvents, such as a solution of sodium hexametaphosphate or ethylene diamine tetraacetic acid (EDTA), that leave the structural polymer intact, thereby resulting in polymeric microspheres. The methyacrylate in the coating embodiment 204 can be removed by soaking the beads in acetone or another solvent that removes the methacrylate without dissolving the outer polymeric shell, resulting in hollow polymeric spheres.

Formation of porous particles is discussed above. To form non-porous beads of suitably small diameter, techniques such as spheronization may be used. Ultimately, the size of the hollow polymeric microspheres can be controlled by the size of the preformed beads and the thickness of the polymeric layer.

Spheronization techniques, which are well-characterized in the art, generate beads that have low surface to volume ratios and smooth surfaces, to allow for the application of uniform layer of the structural polymer. A device called a spheronizer comprises a rotating frictional plate enclosed within a hollow cylinder with a slim clearance between the edges of the rotating base plate and the cylinder wall. Spheronization typically begins with damp extruded particles, such as particles generated by grinding an agglomerated mass of a soluble polymer, such as methacrylate. The extruded particles are broken into uniform lengths and gradually transformed into spherical shapes while rotating on the base plate of the spheronizer. The resulting spherical beads have low surface to volume ratios and smooth surfaces to achieve even coating of the structural polymer on the surfaces thereof.

In still another embodiment, the beads are ice crystals. The ice crystals are removed simply by exposing the microspheres to elevated temperatures.

The invention is illustrated further by the following non-limiting examples.

EXAMPLE 1

An aqueous solution of 2% sodium alginate was infused through a droplet generator directly into a 2% $CaCl_2$ bath. The parameters used for the droplet generator were a nozzle 300 microns in diameter; a flow rate of 10 ml/min; and a frequency of 260 Hz. The $CaCl_2$ solution was decanted and the resulting calcium alginate beads were soaked overnight in an 8% polyvinyl alcohol (PVA) aqueous solution accompanied by slow stirring. The PVA-infused beads were subsequently recovered using a sieve and crosslinked by soaking the beads in a mixture of 3% formaldehyde/20% sulfuric acid at 60° C. for 20 minutes. The alginate was removed from the beads by soaking the beads in 5% sodium hexametaphosphate for 1 hour, resulting in PVA microspheres of 600 microns diameter.

The absence of non-gelling ions resulted in a heterogeneous distribution of the PVA within the particle, with a high concentration at the surface of the particle and a relatively low concentration at the center, resulting in a hollow microsphere.

EXAMPLE 2

A solution of 2% alginate was injected through a droplet generator using a nozzle of 200 micron diameter; a frequency of 660 Hz and a flow rate of 5 ml/min. The droplets were slowly stirred into a solution of 2% $CaCl_2$ solution. The resultant calcium alginate beads were soaked overnight in an 8% polyvinyl alcohol solution, sieved and recovered. The polyvinyl alcohol was crosslinked by soaking the beads in a solution of 4% formaldehyde/20% sulfuric acid at 60° C. for 25 minutes. The alginate was removed by soaking the beads in a 5% sodium hexametaphosphate solution at room temperature, resulting in PVA microspheres of 400 microns diameter.

The absence of non-gelling ions resulted in a heterogeneous distribution of the PVA within the particle, with a high concentration at the surface of the particle and a relatively low concentration at the center, resulting in a hollow microsphere.

What is claimed is:

1. A method for producing spherical polymeric particles, the method comprising the steps of:
   generating spherical beads of a desired size from a starting material comprising a template polymer;
   diffusing a structural polymer into the beads; and
   crosslinking the structural polymer, thereby producing polymeric spherical particles.

2. The method of claim 1, wherein the generating step comprises use of a droplet generator.

3. The method of claim 1, wherein the generating step comprises spheronization.

4. The method of claim 1, wherein the beads are porous.

5. The method of claim 4, wherein the beads comprise a template polymer selected from the group consisting of alginate, polysaccharide, carrageenan, chitosan, hyaluronic acid, and carboxylic-, sulfate-, or amine-functionalized polymers.

6. The method of claim 2, wherein the generating step comprises (i) forming droplets by forcing a mixture comprising the template polymer and a solvent through the droplet generator, and (ii) depositing the droplets into a gelling solution comprising gelling ions to solidify the droplets into beads, the beads having a porosity gradient.

7. The method of claim 6, wherein the solvent does not affect crosslinking of the structural polymer.

8. The method of claim 6, wherein the gelling solution further comprises non-gelling ions to limit the porosity gradient.

9. The method of claim 6, wherein the gelling solution does not contain non-gelling ions so as not to limit the porosity gradient.

10. The method of claim 1, wherein diffusing comprises soaking the beads in a solution comprising the structural polymer.

11. The method of claim 1, further comprising the step of removing the template polymer subsequent to the crosslinking step by subjecting the spherical polymeric particles to a solvent selective for the template polymer only.

12. The method of claim 11, wherein the solvent comprises a solution of sodium hexametaphosphate.

13. The method of claim 11, wherein the solvent comprises a solution of ethylene diamine tetraacetic acid.

14. The method of claim 11, wherein the solvent comprises acetone.

15. The method of claim 1, wherein the resulting polymeric spherical particles are in the range of 1–50 microns diameter.

16. The method of claim 1, wherein the resulting polymeric spherical particles are in the range of 50–100 microns diameter.

17. The method of claim 1, wherein the resulting polymeric spherical particles are in the range of 100–600 microns diameter.

18. The method of claim 1, wherein the resulting polymeric spherical particles are in the range of 600–1000 microns diameter.

19. The method of claim 1, wherein the template polymer is a shape-forming agent.

20. The method of claim 1, wherein the structural polymer is selected from the group consisting of polyvinyl alcohol, polyacrylamide, polyethylene glycol, polyamides, polyureas, polyurethanes, and derivatives thereof.

21. The method of claim 1, wherein the crosslinking step comprises application of a crosslinking agent.

22. The method of claim 21, wherein the crosslinking agent forms covalent bonds with the structural polymer.

23. The method of claim 1, wherein the crosslinking step comprises application of radiation.

24. The method of claim 21, wherein the starting material comprises the crosslinking agent.

25. A method for producing spherical polymeric particles, the method comprising:
   generating spherical beads of a desired size from a starting material comprising a methacrylate template polymer;
   contacting the beads with a structural polymer; and
   crosslinking the structural polymer, thereby producing spherical polymeric particles.

26. The method of claim 25, wherein the beads further comprise a filler agent.

27. The method of claim 26, wherein the filler agent is starch.

28. The method of claim 25, wherein the beads are substantially non-porous.

29. A method for producing spherical polymeric particles comprising the steps of:
   generating ice beads;
   contacting the beads with a structural polymer; and
   crosslinking the structural polymer, thereby producing polymeric spherical particles.

30. The method of claim 29, further comprising the step of removing the ice subsequent to the crosslinking step by exposing the particles to an elevated temperature.

31. The method of claim 29, wherein the contacting step comprises coating the beads with the structural polymer.

32. The method of claim 29, wherein the structural polymer is selected from the group consisting of polyvinyl alcohol, polyacrylamide, polyethylene glycol, polyamides, polyureas, polyurethanes, and derivatives thereof.

33. A method, comprising:
   contacting a template polymer with a structural polymer to form a particle comprising the template polymer and the structural polymer; and
   removing at least a portion of the template polymer from the particle.

34. The method of claim 33, further comprising, after contacting the template polymer and the structural polymer but before removing the portion of the template polymer, cross-linking the structural polymer.

35. The method of claim 34, wherein cross-linking the structural polymer includes contacting the structural polymer with a cross-linking agent.

36. The method of claim 35, wherein the cross-linking agent is selected from the group consisting of formaldehyde and glutaraldehyde.

37. The method of claim 33, further comprising, before contacting the template polymer with the structural polymer, forming droplets of the template polymer.

38. The method of claim 37, wherein forming the droplets of the template polymer includes passing a solution containing the template polymer through a nozzle.

39. The method of claim 38, wherein passing the solution containing the template polymer through the nozzle forms a stream containing the template polymer.

40. The method of claim 39, further comprising subjecting the nozzle to a periodic disturbance to break up the stream containing the template polymer.

41. The method of claim 33, wherein the template polymer comprises a polysaccharide.

42. The method of claim 41, wherein the polysaccharide comprises alginate.

43. The method of claim 33, wherein the template polymer is selected from the group consisting of carrageenans, chitosan, hyaluronic acid, carboxylic-functionalized polymers, sulfate-functionalized polymers, amine-functionalized polymers, blends thereof, and derivatives thereof.

44. The method of claim 33, wherein the structural polymer is selected from the group consisting of vinyl polymers, polyacrylamides, polyethylene glycols, polyamides, polyureas, polyurethanes, polyvinyl alcohols, and derivatives thereof.

45. The method of claim 44, wherein the structural polymer comprises a polyvinyl alcohol.

46. The method of claim 33, wherein the particle has a diameter of less than 600 microns.

47. The method of claim 46, wherein the particle has a diameter of 1 to 50 microns.

48. The method of claim 46, wherein the particle has a diameter of 50 to 100 microns.

49. The method of claim 46, wherein the particle has a diameter of 100 to 600 microns.

50. The method of claim 33, wherein the particle has a diameter of 600 to 1000 microns.

51. The method of claim 33, wherein the template polymer comprises alginate, the structural polymer comprises a polyvinyl alcohol, and the particle has a diameter of less than 600 microns.

52. A method, comprising:
contacting a first polymer with a second polymer to form a particle comprising the first and second polymers; and
removing at least a portion of the first polymer from the particle,
wherein the particle has a diameter of about 1000 microns or less.

53. The method of claim 52, wherein the first polymer comprises a polysaccharide.

54. The method of claim 53, wherein the polysaccharide comprises alginate.

55. The method of claim 52, wherein the first polymer is selected from the group consisting of carrageenans, chitosan, hyaluronic acid, carboxylic-functionalized polymers, sulfate-functionalized polymers, amine-functionalized polymers, blends thereof, and derivatives thereof.

56. The method of claim 52, wherein the second polymer is selected from the group consisting of vinyl polymers, polyacrylamides, polyethylene glycols, polyamides, polyureas, polyurethanes, polyvinyl alcohols, and derivatives thereof.

57. The method of claim 52, wherein the second polymer comprises a polyvinyl alcohol.

* * * * *